(12) United States Patent
Licari et al.

(10) Patent No.: US 8,618,085 B2
(45) Date of Patent: Dec. 31, 2013

(54) THERAPEUTIC FORMULATIONS OF DESOXYEPOTHILONES

(75) Inventors: Peter J. Licari, Fremont, CA (US); Ziyang Zhong, Union City, CA (US); Indu Isaacs, Andover, MA (US); John G. Augustine, Lynn, MA (US)

(73) Assignee: Koasn Biosciences Incorporated, Hayward, CA (US)

( * ) Notice: Subject to any disclaimer, the term of this patent is extended or adjusted under 35 U.S.C. 154(b) by 2203 days.

(21) Appl. No.: 11/082,053

(22) Filed: Mar. 15, 2005

(65) Prior Publication Data

US 2005/0277682 A1 Dec. 15, 2005
US 2010/0137382 A9 Jun. 3, 2010

Related U.S. Application Data

(63) Continuation-in-part of application No. 09/957,483, filed on Sep. 19, 2001, now Pat. No. 6,998,256, which is a continuation-in-part of application No. PCT/US01/13793, filed on Apr. 26, 2001, which is a continuation-in-part of application No. 09/825,876, filed on Apr. 3, 2001, now Pat. No. 6,589,968, and a continuation-in-part of application No. 09/825,856, filed on Apr. 3, 2001, now Pat. No. 6,489,314, and a continuation-in-part of application No. 09/560,367, filed on Apr. 28, 2000, now Pat. No. 6,410,301.

(60) Provisional application No. 60/564,197, filed on Apr. 20, 2004, provisional application No. 60/232,696, filed on Sep. 14, 2000, provisional application No. 60/257,517, filed on Dec. 21, 2000, provisional application No. 60/269,020, filed on Feb. 13, 2001.

(51) Int. Cl.
*A61K 31/33* (2006.01)

(52) U.S. Cl.
USPC ........................................................ 514/183

(58) Field of Classification Search
USPC .......................................................... 514/183
See application file for complete search history.

(56) References Cited

U.S. PATENT DOCUMENTS

| | | | | |
|---|---|---|---|---|
| 5,922,754 | A * | 7/1999 | Burchett et al. | 514/449 |
| 6,204,388 | B1 | 3/2001 | Danishefsky et al. | |
| 6,576,651 | B2 | 6/2003 | Bandyopadhyay et al. | |
| 6,583,290 | B1 * | 6/2003 | Julien et al. | 548/203 |
| 6,660,286 | B1 | 12/2003 | Lambert et al. | |
| 6,867,305 | B2 | 3/2005 | Danishefsky et al. | |
| 7,070,964 | B2 | 7/2006 | Tang et al. | |
| 2002/0058286 | A1 | 5/2002 | Danishefsky et al. | |
| 2003/0073205 | A1 * | 4/2003 | Arslanian et al. | 435/117 |
| 2003/0176368 | A1 | 9/2003 | Danishefsky et al. | |
| 2003/0219877 | A1 | 11/2003 | Tang et al. | |
| 2003/0220378 | A1 | 11/2003 | Lee | |
| 2004/0053995 | A1 | 3/2004 | Danishefsky et al. | |
| 2004/0072882 | A1 | 4/2004 | Johnson, Jr. et al. | |
| 2004/0132692 | A1 | 7/2004 | Sherrill et al. | |
| 2004/0152708 | A1 | 8/2004 | Li et al. | |
| 2004/0247660 | A1 | 12/2004 | Singh | |

FOREIGN PATENT DOCUMENTS

| | | |
|---|---|---|
| WO | 99/39694 A1 | 8/1999 |
| WO | WO 00/71163 A1 | 11/2000 |
| WO | WO 02/26208 A2 | 4/2002 |
| WO | 03/084536 | 10/2003 |
| WO | WO 2004/024126 A1 | 3/2004 |

OTHER PUBLICATIONS

Akers, Michael 'Excipient-Drug Interactions in Parenteral Formulations.' Journal of Pharmaceutical Sciences, vol. 91, No. 11, p. 2283-2300, 2002.*
Strickley, Robert 'Solubilizing Excipients in Oral and Injectable Formulations.' Pharmaceutical Research, vol. 21, No. 2, p. 201-230, 2004.*
Nema et al 'Excipients and Their Use in Injectable Products' PDA Journal of Pharmaceutical Science and Technology, 51(4), 1997, p. 166-171.*
Strickley 'Solubilizing Excipients in Oral and Injectable Formulations' Pharmaceutical Research, 21(2), 2004, p. 201-229.*
U.S. Appl. No. 10/962,308, filed Oct. 8, 2004, Sherrill et al.
Chou, T.C., Zhang, X. G., et al., "Desoxyepothilone B is curative against human tumor xenografts that are refractory to paclitaxel," *Proc Natl Acad Sci USA* 1998 95 (26), 15798-802.
Chou, T.-C., O'Connor, O. A., et al., "The synthesis, discovery, and development of a highly promising class of microtubule stabilization agents: curative effects of desoxyepothilones B and F against human tumor xenografts in nude mice," *Proc. Natl. Acad. Sci. USA* 2001 98 (14), 8113-8118.
Cowden, C. J. and Paterson, I., "Synthetic chemistry. Cancer drugs better than taxol?" *Nature* 1997, 387, 238-9.
Harris, C. R., Balog, A., et al., "Epothilones: microtubule stabilizing agents with enhanced activity against multidrug-resistant cell lines and tumors," *Actualites de Chimie Therapeutique* 1999 25, 187-206.
Harris, C. R., Kuduk, S. D., et al., "New Chemical Synthesis of the Promising Cancer Chemotherapeutic Agent 12,13-Desoxyepothilone B: Discovery of a Surprising Long-Range Effect on the Diasteroselectivity of an Aldol Condensation," *J. Am. Chem. Soc*, 1999 121 (30), 7050-7062.
Martin, N. and Thomas, E. J., "Total syntheses of epothilones B and D: applications of allylstannanes in organic synthesis," *Tetrahedron Letters* 2001 42 (47), 8373-8377.
McDaid et al., "Validation of the Pharmacodynamics of BMS-247550, and Analogue of Epothilone B, during a Phase I Clinical Study," *Clin Cancer Res* 2002 8 (7), 2035-43.
Muhlradt, P. F. and Sasse, F., "Epothilone B stabilizes microtubuli of macrophages like taxol without showing taxol-like endotoxin activity" *Cancer Res.* 1997 57 (16), 3344-6.

(Continued)

*Primary Examiner* — Brandon Fetterolf
*Assistant Examiner* — Christopher R Stone
(74) *Attorney, Agent, or Firm* — Fox Rothschild LLP; Gerard P. Norton; Wansheng Jerry Liu

(57) ABSTRACT

Formulations of desoxyepothilones are stable before and after dilution into aqueous media.

15 Claims, No Drawings

(56) References Cited

OTHER PUBLICATIONS

Su, D.-S., Meng, D., et al., "Total synthesis of (−)—epothilone B: an extension of the Suzuki coupling method and insights into structure-activity relationships of the epothilones," *Ang. Chemie, Int. Ed. Eng.* 1997 36 (7), 757-759.

Akers, Michael J., "Excipient—Drug Interactions in Parenteral Formulations,"; Journal of Pharmaceutical Sciences (Nov. 2002), vol. 91, No. 11, pp. 2283-2300.

Chou et al., "Desoxyepothilone B is Curative Against Human Tumor Xenografts That Are Refractory to Paclitaxel," Proc. Natl. Acad. Sci (Dec. 1998), vol. 95, pp. 15798-15802.

Strickley, Robert G., "Solubilizing Excipients in Oral and Injectable Formulations," Pharmaceutical Research (Feb. 2004), vol. 21, No. 2, pp. 201-224.

Supplementary European Search Report issued on EP05726048.1 (PCT/US05/009541), (2009).

\* cited by examiner

THERAPEUTIC FORMULATIONS OF DESOXYEPOTHILONES

CROSS-REFERENCE TO RELATED APPLICATIONS

This application claims the benefit of U.S. Provisional Application No. 60/564,197, filed Apr. 20, 2004; the disclosure of which is incorporated herein by reference. This application is also a continuation-in-part of U.S. application Ser. No. 09/957,483, filed Sep. 19, 2001, now U.S. Pat. No. 6,998,256, which is a continuation-in-part of Application No. PCT/US01/13793, filed Apr. 26, 2001, which is a continuation-in-part of application Ser. Nos. 09/825,876 and 09/825,856, both filed Apr. 3, 2001, now U.S. Pat. Nos. 6,589,968 and 6,489,314, respectively, and a continuation-in-part of application Ser. No. 09/560,367, filed Apr. 28, 2000, now U.S. Pat. No. 6,410,301, and claims benefits under 35 U.S.C. §119(e) of U.S. Provisional Application No. 60/269,020, filed Feb. 13, 2001, Provisional Application No. 60/257,517, filed Dec. 21, 2000, and Provisional Application No. 60/232,696, filed Sep. 14, 2000.

BACKGROUND OF THE INVENTION

1. Field of the Invention

This invention relates to pharmaceutical formulations of desoxyepothilones and methods for their preparation and use.

2. Description of Related Art

The class of polyketides known as epothilones has emerged as a source of potentially therapeutic compounds having modes of action similar to paclitaxel (see, e.g., Cowden, C. J. and Paterson, I., "Synthetic chemistry. Cancer drugs better than taxol?" *Nature* 1997, 387, 238-9). Interest in the epothilones and epothilone analogs has grown with the observations that certain epothilones are active against tumors that have developed resistance to paclitaxel (Harris, C. R., Balog, A., et al., "Epothilones: microtubule stabilizing agents with enhanced activity against multidrug-resistant cell lines and tumors," *Actualites de Chimie Therapeutique* 1999 25, 187-206) as well as reduced potential for undesirable side-effects (Muhlradt, P. F. and Sasse, F., "Epothilone B stabilizes microtubuli of macrophages like taxol without showing taxol-like endotoxin activity" *Cancer Res.* 1997 57 (16), 3344-6). Among the epothilones and epothilone analogs being investigated for therapeutic efficacy are epothilone B and the semi-synthetic epothilone B analogs, BMS-247550, also known as "azaepothilone B" (see, e.g., McDaid et al., "Validation of the Pharmacodynamics of BMS-247550, an Analogue of Epothilone B, during a Phase I Clinical Study," *Clin Cancer Res* 2002 8 (7), 2035-43), and BMS-310705.

Desoxyepothilone B (1), also known as "epothilone D" is another epothilone derivative having promising anti-tumor properties viz. paclitaxel that is being investigated for therapeutic efficacy (Su, D.-S., Meng, D., et al., "Total synthesis of (−)-epothilone B: an extension of the Suzuki coupling method and insights into structure-activity relationships of the epothilones," *Ang. Chemie, Int. Ed. Eng.* 1997 36 (7), 757-759; Chou, T. C., Zhang, X. G., et al., "Desoxyepothilone B is curative against human tumor xenografts that are refractory to paclitaxel," *Proc Natl Acad Sci USA* 1998 95 (26), 15798-802; Harris, C. R., Kuduk, S. D., et al., "New Chemical Synthesis of the Promising Cancer Chemotherapeutic Agent 12,13-Desoxyepothilone B: Discovery of a Surprising Long-Range Effect on the Diastereoselectivity of an Aldol Condensation," *J. Am. Chem. Soc.* 1999 121 (30), 7050-7062.; Chou, T.-C., O'Connor, O. A., et al., "The synthesis, discovery, and development of a highly promising class of microtubule stabilization agents: curative effects of desoxyepothilones B and F against human tumor xenografts in nude mice," *Proc. Natl. Acad. Sci. USA* 2001 98 (14), 8113-8118; Danishefsky et al. US 2002/0058817 A1 (2002); Martin, N. and Thomas, E. J., "Total syntheses of epothilones B and D: applications of allylstannanes in organic synthesis," *Tetrahedron Letters* 2001 42 (47), 8373-8377; and Danishefsky et al. US 2002/0058286 A1 (2002)). This compound has also demonstrated less toxicity than epothilones having 12, 13-epoxides, such as epothilone B or BMS-247550.

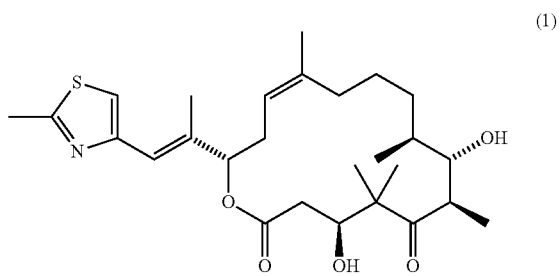

(1)

The epothilones in general, and the desoxyepothilones in specific, have poor aqueous solubility; and current epothilone formulations typically include a castor oil derivative solubilizing agent sold under the trade name CREMOPHOR® (polyethoxylated castor oil; BASF Aktiengesellschaft) to enhance solubility. CREMOPHOR® has been associated with patient discomfort and toxicity, in part due to allergic reactions. Therefore, it would be preferable to provide enhanced formulations of desoxyepothilones that do not require CREMOPHOR®. Further, the 16-member ring system of desoxyepothilones is susceptible to hydrolytic degradation upon storage in aqueous media. There is thus an unmet need for formulations of desoxyepothilones that are chemically and physically stable to long-term storage and that provide chemically and physically stable, well-tolerated solutions upon dilution into aqueous media prior to administration.

BRIEF SUMMARY OF THE INVENTION

In one aspect, the present invention provides pharmaceutical concentrates for use in preparing pharmaceutical compositions useful in treating proliferative disease, typically, but not necessarily, in a mammal, preferably in a human. In one embodiment, the present invention provides a pharmaceutical concentrate comprising a desoxyepothilone and a pharmaceutically acceptable carrier, embodiments of which carrier will be described in greater detail herein below. The pharmaceutical concentrates of the invention are chemically and physically stable to storage under standard conditions and provide homogeneous solutions upon appropriate dilution into aqueous medium prior to administration.

In particular embodiments of the invention, the pharmaceutical concentrate of the invention includes at least one alcohol. In more particular embodiments of the pharmaceutical concentrates provided by the invention, the alcohol is a water-miscible alcohol such as ethanol.

In other particular embodiments of the invention, the pharmaceutical concentrate of the invention includes at least one glycol. In more particular embodiments of the pharmaceutical concentrates provided by the invention, the glycol is a compound such as glycerol or propylene glycol.

In other particular embodiments of the invention, the pharmaceutical concentrate of the invention includes at least one polyol. In more particular embodiments of the pharmaceutical concentrates provided by the invention, the polyol is a poly($C_2$-$C_3$)alkylene glycol.

In other particular embodiments of the the invention, the pharmaceutical concentrate of the invention includes at least one surfactant, such as a polyoxyethylene sorbitan monoester like polysorbate 80 (polyoxyethylenesorbitol monooleate, Tween® 80, BASF Aktiengesellschaft) or Solutol® HS-15 (polyoxyethyleneglycol 660 hydroxystearate, BASF Aktiengesellschaft).

In other particular embodiments of the invention, the pharmaceutical concentrate of the invention includes at least one organic solvent, such as dimethylacetamide or an N-alkylpyrrolidinone, such as N-methylpyrrolidinone, or methylsulfoxide (DMSO).

In particular embodiments of the invention, the pharmaceutical concentrate of the invention comprises a desoxyepothilone at a concentration of up to about 100 mg/mL. In more particular embodiments of the invention, the pharmaceutical concentrate of the invention comprises a desoxyepothilone at a concentration of between about 1 mg/mL and about 20 mg/mL. In more particular embodiments of the invention, the pharmaceutical concentrate of the invention comprises a desoxyepothilone at a concentration of between about 1 mg/mL and about 10 mg/mL. In even more particular embodiments of the invention, the pharmaceutical concentrate of the invention comprises epothilone D at a concentration of about 8-10 mg/mL.

In another aspect, the invention provides pharmaceutical compositions ready for administration to a subject in need to treatment, prepared by dilution of the above-described pharmaceutical concentrates into aqueous medium. The pharmaceutical compositions provide a desoxyepothilone in a therapeutically effective concentration, and the pharmaceutical compositions are effective to deliver a therapeutically effective amount of desoxyepothilone.

In another aspect of the invention, the pharmaceutical compositions provided are used to treat proliferative diseases sensitive to desoxyepothilones. In particular embodiments, the proliferative disease is cancer. In more particular embodiments, the cancer is selected from the group consisting of breast cancer, including metastatic breast cancer, bladder cancer, colorectal cancer, including metastatic colon cancer, non-small cell lung cancer, prostate cancer, cancers of the head and neck, cholangiocarcinoma, soft tissue sarcoma, gastric cancer, hepatocellular cancer, renal cancer, ovarian cancer, lymphoma, and brain cancer.

In other embodiments, the pharmaceutical compositions provided are used to treat non-cancer diseases characterized by cellular proliferation (e.g., psoriasis, multiple sclerosis, rheumatoid arthritis, atherosclerosis, and the like).

In other embodiments, the invention provides pharmaceutical compositions effective to provide therapeutically effective dosage levels of a desoxyepothilone to a patient in need of such treatment. In particular embodiments, the composition is effective at providing a dosage level between about 0.1 mg/m² and about 200 mg/m².

DETAILED DESCRIPTION OF THE INVENTION

In one aspect, the present invention provides pharmaceutical concentrates for use in preparing pharmaceutical compositions useful in treating proliferative disease, typically, but not necessarily, in a mammal, preferably in a human. In one embodiment, the present invention provides a pharmaceutical concentrate comprising a desoxyepothilone and a pharmaceutically acceptable carrier, embodiments of which carrier will be described in greater detail herein below. The pharmaceutical concentrates of the invention are chemically and physically stable to storage under standard conditions and provide homogeneous solutions upon appropriate dilution into aqueous medium prior to administration.

The term "desoxyepothilone" as used herein encompasses compounds of the general formula (I),

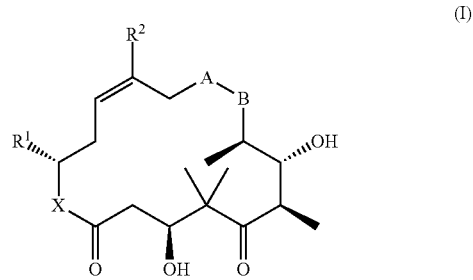

wherein
R¹ is aryl, heteroaryl, or a group of the formula

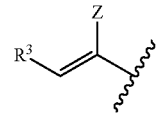

wherein R³ is aryl or heteroaryl, and Z is H, Me, or F;
R² is H or $C_1$-$C_4$ alkyl;
X is O or NH; and
A-B is $CH_2$—$CH_2$ or trans-CH=CH.

The term "aryl" as used herein encompasses aromatic monocyclic or polycyclic hydrocarbyl groups, for example phenyl, naphthyl, and the like, and includes both unsubstituted and substituted forms thereof. The term "heteroaryl" as used herein encompasses aromatic monocyclic or polycyclic groups comprising one or more non-carbon atoms, for example pyridyl, pyrimidinyl, quinolyl, imidazolyl, oxazolyl, thiazolyl, benzothiazolyl, isoxazolyl, isothiazolyl, and the like, and includes both unsubstituted and substituted forms thereof. The term "alkyl" as used herein encompasses linear, branched, and cyclic saturated hydrocarbyl groups, and includes both unsubstituted and substituted forms thereof. Examples of substituents on each of the above-defined groups include but are not limited to halogen, alkyl, alkoxy, aryl, heteroaryl, carboxy, carbonyl, oxo, carboxamido, nitro, cyano, azido, amino, alkylamino, dialkylamino, hydroxy, and alkylthio groups.

In particular embodiments of the invention,
R¹ is a group of the formula

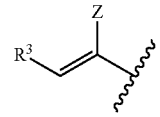

wherein R³ is aryl or heteroaryl, and Z is Me;
R² is $CH_3$ or $CF_3$,
A-B is $CH_2$—$CH_2$ or trans-CH=CH, and
X is O.

In more particular embodiments of the invention,
R¹ is a group of the formula

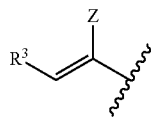

wherein R³ is 4-thiazolyl, 2-methyl-4-thiazolyl, 2-(hydroxymethyl)-4-thiazolyl, 2-(aminomethyl)-4-thiazolyl, 2-pyridyl, 2-quinolyl, 2-benzothiazolyl, 4-oxazolyl, 2-methyl-4-oxazolyl, 3-isoxazolyl, or methylisoxazolyl, and Z is Me;

R² is $CH_3$ or $CF_3$,

A-B is $CH_2$—$CH_2$ or trans-CH═CH, and

X is O.

In more particular embodiments of the invention, the desoxyepothilone is epothilone D.

In one embodiment, the invention provides compositions in the form of concentrates comprising a desoxyepothilone together with a pharmaceutically acceptable carrier. These concentrates comprise no additional water beyond that normally present in the individual components. Said concentrates are chemically and physically stable to storage at or below ambient temperatures, and provide homogeneous aqueous solutions for a sufficient period of time when diluted into aqueous medium, e.g. water, saline, or aqueous dextrose, prior to administration to a patient. For the purposes of the present invention, the concentrates and their aqueous dilutions are said to be physically stable when there is no observed change in physical form; for example, a physically stable concentrate or aqueous dilution does not undergo phase separation, for example crystallization or precipitation of one or more components or separation into multiple immiscible liquid phases, during the period of physical stability. By "ambient temperatures" is meant temperatures between about 10° C. and about 40° C., preferably between about 15° C. and about 35° C., and most preferably about 25° C. Further, for the purposes of the present invention, the desoxyepothilone is said to be chemically stable in the concentrate or in the aqueous dilution when it retains at least 95% purity upon analysis after an indicated period of time.

In one embodiment of the invention, the concentrates provide homogeneous aqueous solutions for up to about 48 hours when diluted up to about 10-fold (v/v) into an aqueous medium, for example water, aqueous dextrose, or saline. In another embodiment of the invention, the concentrates provide homogeneous aqueous solutions for up to about 24 hours when diluted from about 5-fold (v/v) up to about 10-fold (v/v) into aqueous medium.

The pharmaceutically acceptable carrier may be selected from any such carrier known in the art, and may be used individually or in combination with other pharmaceutically acceptable carriers. Examples of pharmaceutically acceptable carriers include but are not limited to simple alcohols, for example ethanol; glycols, for example glycerol and propylene glycol; polyols, for example poly($C_2$-$C_3$)alkylene glycols such as polyethylene glycols (PEG) like PEG 400 or PEG 600; cyclodextrins such as β-cyclodextrin, hydroxypropyl-β-cyclodextrin, and sulfopropyl-β-cyclodextrin (Captisol®, CyDex); surfactants, such as polyoxyethylene sorbitan monoesters like polysorbate 80 (polyoxyethylene sorbitol monooleate, TWEEN® 80, BASF Aktiengesellschaft), polysorbate 60 (polyoxyethylene sorbitol monosterate, TWEEN® 60, BASF Aktiengesellschaft), polysorbate 40 (polyoxyethylene sorbitol monopalmitate, TWEEN® 40, BASF Aktiengesellschaft), or polysorbate 20 (polyoxyethylene sorbitol monolaurate, TWEEN® 20, BASF Aktiengesellschaft), and Solutol® HS-15 (polyethylene glycol hydroxystearate, BASF Aktiengesellschaft); and organic solvents, such as dimethylacetamide and N-methylpyrrolidinone.

In certain embodiments of the invention, the pharmaceutical concentrates comprise a desoxyepothilone dissolved in a pharmaceutically acceptable carrier comprising an alcohol, a glycol, a polyol, and a surfactant. In certain particular embodiments of the invention, the alcohol is ethanol, the glycol is selected from the group consisting of glycerol and propylene glycol, the polyol is a polyethylene glycol of molecular weight between about 200 and about 600 Daltons, and the surfactant is a polyoxyethylene sorbitan monoester. In certain particular embodiments of the invention, the pharmaceutically acceptable carriers comprise between about 40% (v/v) and about 70% (v/v) ethanol, between about 5% (v/v) and about 20% (v/v) glycerol, between about 5% (v/v) and about 20% (v/v) polysorbate 80, and between about 5% (v/v) and about 30% (v/v) polyethylene glycol. In certain more particular embodiments of the invention, the pharmaceutically acceptable carrier comprises about 60% (v/v) ethanol, about 10% (v/v) glycerol, about 10% (v/v) PEG 400, and about 10% (v/v) polysorbate 80. In other more particular embodiments of the invention, the pharmaceutically acceptable carrier comprises about 50% (v/v) ethanol, about 10% (v/v) propylene glycol, about 30% (v/v) PEG 400, and about 10% (v/v) polysorbate 80.

In certain particular embodiments of the invention, the alcohol is ethanol, the glycol is selected from the group consisting of glycerol and propylene glycol, the polyol is a polyethylene glycol of molecular weight between about 200 and about 600 Daltons, and the surfactant is Solutol® HS-15. In certain particular embodiments of the invention, the pharmaceutically acceptable carriers comprise between about 40% (v/v) and about 80% (v/v) ethanol, between about 10% (v/v) and about 40% (v/v) Solutol® HS-15, and between about 5% (v/v) and about 40% (v/v) polyethylene glycol. In certain more particular embodiments of the invention, the pharmaceutically acceptable carrier comprises about 50% (v/v) ethanol, about 30% (v/v) PEG400, and about 20% (v/v) Solutol® HS-15. In other more particular embodiments of the invention, the pharmaceutically acceptable carrier comprises about 65% (v/v) ethanol, about 10% (v/v) PEG400, and about 25% (v/v) Solutol® HS-15.

In certain embodiments of the invention, the desoxyepothilone is dissolved in one of the above-described pharmaceutically acceptable carriers at a concentration of between about 0.1 mg/mL and about 100 mg/mL. In particular embodiments of the invention, the desoxyepothilone is dissolved in one of the above-described pharmaceutically acceptable carriers at a concentration of between about 1 mg/mL and about 50 mg/mL In more particular embodiments of the invention, the desoxyepothilone is dissolved in one of the above-described pharmaceutically acceptable carriers at a concentration of between about 1 mg/mL and about 10 mg/mL. In even more particular embodiments of the invention, the desoxyepothilone is dissolved in one of the above-described pharmaceutically acceptable carriers at a concentration of between about 8 mg/mL and about 10 mg/mL.

The above-described pharmaceutical concentrates are preferably prepared in sterile form, for example by filtration of said formulation through sterile filtration membranes, for example using a 0.2-micron filter. Aseptic formulation of any composition in liquid form, preparation and filling of aseptic vials, and dilution and/or combining of liquids for parenteral use under aseptic conditions are well known to those skilled in the art.

The pharmaceutical concentrates of the invention may be placed in any convenient container, for example vials, double-chamber vial systems, or ampoules, made of materials that are non-reactive towards said formulations. Typically, the containers are made of glass, for example borosilicate or soda-lime glass, which may be colorless or tinted so as to prevent photo-decomposition. The vials may be of any volume conventional in the art, and preferably are of a size sufficient to accommodate 1 to 10 mL of the concentrate. More preferably, the vials are of a size sufficient to accommodate the concentrate as well as the diluent required for preparation of the pharmaceutical composition suitable for parenteral administration. The containers may preferably accommodate a closure that can be pierced, for example a sterile rubber stopper or septum cap that may allow for transfer of liquid into or out of the container under sterile conditions. The containers may be filled with an inert atmosphere, for example using nitrogen or argon gas, to retard oxidative degradation upon storage.

A pharmaceutical composition of the present invention in suitable form for parenteral administration may be obtained by suitable dilution of the above-described concentrates into sterile water, saline, or aqueous dextrose. In one embodiment of the invention, the concentrate is diluted 1:5 or 1:10 (v/v) into sterile filtered water for injection (WFI), 5% aqueous dextrose, 0.9% saline, or 0.45% saline.

The compositions of the invention may be prepared by dissolving any suitable form of the desoxyepothilone, for example crystalline or amorphous solid forms such as lyophilates, in the carrier followed by sterile filtration into the appropriate containers as described above. In one embodiment of the invention, the desoxyepothilone is first dissolved in a first excipient to provide a concentrated stock solution that is dispensed into a suitable container so as to provide the appropriate quantity of epothilone. The remaining excipients are then added to the container in the appropriate amounts with sufficient mixing, and the final composition is sterile filtered into the final vials. In one particular embodiment of the invention, the desoxyepothilone is first dissolved in ethanol at a concentration of between about 10 mg/mL and about 100 mg/mL, and appropriate aliquots are transferred into the final vials so as to provide the desired final amount of the desoxyepothilone. The other excipients are added in a sequence such that homogeneous solutions are formed. The appropriate order of addition of excipients may be readily determined by one of skill in the art.

The stability of the desoxyepothilone formulations before or after dilution into aqueous medium is readily determined, for example by visual inspection for formation of precipitates or crystallization or for phase separation as illustrated in Example 4 below. Alternatively, automated or semi-automated techniques based on light scattering may be used. The formulations may also be examined using osmometry as illustrated in Example 5 below. The stability of the desoxyepothilone in the formulations of the invention is readily determined, for example by HPLC analysis as illustrated in Example 1 below.

The invention is illustrated by way of the following examples, which are not intended to limit the scope of the invention.

EXAMPLE 1

HPLC Analysis of Epothilone D

Epothilone D was assayed using HPLC as follows. Mobile phase A consisted of 450 mL of water (purified by reverse osmosis), 550 mL of acetonitrile (HPLC grade), and 1.25 mL of glacial acetic acid. Mobile phase B consisted of 100 mL of water (purified by reverse osmosis), 900 mL of acetonitrile (HPLC grade), and 1.0 mL of glacial acetic acid. A 1 mg/mL reference standard of epothilone D was prepared by dissolving 10 mg of epothilone D in 10 mL of methanol. Diluted standard samples were prepared by dilution of this 1 mg/mL reference standard into methanol. Chromatography was performed using a Hewlett-Packard 1100 HPLC system fitted with a ZORBAX 4.6×150 mm Eclipse® C8 column (Agilent), using a flow rate of 1.0 mL/min at a column temperature of 35° C. and using UV detection at 250 nm, with a 4 nm bandwidth and using 360 nm as reference. A solvent gradient was run over 35 minutes as follows: t=0 min, % B=0; t=12 min, % B=0%; t=14 min, % B=100%; t=20 min, % B=100%; t=22 min, % B=0%; t=35 min, % B=0%. Under these conditions, epothilone D eluted at 10.1 minutes. Minor impurities were found to elute as follows: epothilone C, 8.0 min; 10,11-dehydroepothilone D, 8.9 min; epothilone $C_{10}$, 11.9 min. The epothilone D was quantitated using the area under the UV peak by comparison with a standard curve. This quantitative method provided a relative error of ≤2.2% using 6 injections of 6 separate preparations of an 0.4 mg/mL solution. Injection error was found to be ≤0.3% using 6 injections of the same 0.4 mg/mL solution. Analysis of a series of standard solutions showed linearity at least between 1 and 10 µg of epothilone D per injection. The lower limit of detection for epothilone D was 0.08 µg and the lower limit of quantitation was 0.23 microgram of epothilone D using this method.

EXAMPLE 2

Characterization of Epothilone D

Epothilone D (lot # K360-38-A) was analyzed by modulated differential scanning calorimetry (MDSC) to confirm the melting temperature and homogeneity of the material. Epothilone D (9.5 mg) was placed in an aluminum pan and sealed with an aluminum lid. The sample was placed in the MDSC cell (MDSC 2920, TA Instruments) and ramped from 20° C. to 170° C. using the following program: (1) equilibrate at 20.00° C.; (2) isothermal for 5.00 min; (3) modulate ±1.00° C. every 60 seconds; (4) data storage on; (5) ramp 1.00° C./min to 200.00° C.; (6) equilibrate at 200.00° C.; (7) isothermal for 5.00 min; (8) data storage off; (9) ramp 10.00° C./min to 20.00° C.; (10) end of method. The resulting thermogram showed a single melting transition at 122.6° C. A glass transition temperature was observed at ~66° C., as well.

EXAMPLE 3

Epothilone D Solubility in Various Formulations

A stock solution of epothilone D (100 mg/mL) was prepared in ethanol. Epothilone D formulations containing 10 mg/mL of epothilone D were prepared as listed in the following tables by addition of the requisite amount of ethanol, propylene glycol, glycerol, PEG400, and/or Tween® 80 to the appropriate volume of the epothilone D stock solution. The solubility of epothilone D in each vial was observed visually following gentle swirling. Each formulation was syringe filtered through a 0.2 micron PVDF (polyvinylidene fluoride) filter. Each formulation was subsequently diluted 1:10 in reverse osmosis deionized water (RODI), 5% dextrose (D5W), or 0.9% saline. Visual observations were taken upon preparation, upon dilution, and both 1 and 19 or 30 hours after incubation at ambient temperature. Solutions either remained clear ("clear") or precipitation ("ppt") or crystallization ("xtal") was observed.

In one experiment, the effects of varying the proportions of ethanol (EtOH) and propylene glycol (PG) with constant 10% Tween® 80 in formulations containing 10 mg/mL of epothilone D were determined as shown in Table 1. (In Table 1 and subsequent tables, all percents are volume percents.)

TABLE 1

Epothilone D solubility in 10 mg/mL formulations with 10% Tween® 80 and varying ethanol and propylene glycol concentrations

| For- | % | % | Visual Appearance | | | | | | |
|---|---|---|---|---|---|---|---|---|---|
| | | | | RODI | | D5W | | Saline | |
| mula-tion | EtOH | PG | Ini-tial | 1 h | 19 h | 1 h | 19 h | 1 h | 19 h |
| A | 80 | 10 | clear | clear | clear | clear | clear | clear | clear |
| B | 70 | 20 | clear | clear | clear | clear | xtal | clear | xtal |
| C | 60 | 30 | clear | clear | clear | clear | xtal | clear | xtal |
| D | 50 | 40 | clear | clear | clear | clear | clear | clear | clear |
| E | 40 | 50 | clear | clear | clear | clear | clear | clear | clear |
| F | 30 | 60 | clear | clear | xtal | clear | xtal | clear | clear |
| G | 20 | 70 | ppt | — | — | — | — | — | — |
| H | 10 | 80 | ppt | — | — | — | — | — | — |

Key: "ppt" = precipitation; "xtal" = crystallization

In another experiment, the effects of varying the proportions of ethanol (EtOH) and PEG400 (PEG) with constant 10% Tween® 80 in formulations containing 10 mg/mL of epothilone D were determined as shown in Table 2.

TABLE 2

Epothilone D solubility in 10 mg/mL formulations with 10% Tween® 80 and varying ethanol and PEG400 concentrations

| For- | % | % | Visual Appearance | | | | | | |
|---|---|---|---|---|---|---|---|---|---|
| | | PEG | | RODI | | D5W | | Saline | |
| mula-tion | EtOH | 400 | Initial | 1 h | 19 h | 1 h | 19 h | 1 h | 19 h |
| A | 80 | 10 | clear | clear | xtal | clear | xtal | clear | xtal |
| B | 70 | 20 | clear | clear | xtal | clear | xtal | clear | xtal |
| C | 60 | 30 | clear | clear | xtal | clear | xtal | clear | xtal |
| D | 50 | 40 | clear | clear | xtal | clear | xtal | clear | xtal |
| E | 40 | 50 | clear | clear | xtal | clear | xtal | clear | xtal |
| F | 30 | 60 | clear | clear | clear | clear | clear | clear | xtal |
| G | 20 | 70 | clear | clear | clear | clear | clear | clear | xtal |
| H | 10 | 80 | clear | clear | clear | clear | xtal | clear | xtal |

Key: "ppt" = precipitation; "xtal" = crystallization

In another experiment, the effects of varying the proportions of Tween® 80 and propylene glycol (PG) with constant 60% ethanol in formulations containing 10 mg/mL of epothilone D were determined as shown in Table 3.

TABLE 3

Epothilone D solubility in 10 mg/mL formulations with 60% ethanol and varying Tween® 80 and propylene glycol concentrations

| For- | % | % | Visual Appearance | | | | | | |
|---|---|---|---|---|---|---|---|---|---|
| | Tween | | | RODI | | D5W | | Saline | |
| mula-tion | 80 | PG | Initial | 1 h | 19 h | 1 h | 19 h | 1 h | 19 h |
| A | 10 | 30 | clear | clear | xtal | clear | clear | clear | xtal |
| B | 11 | 29 | clear | clear | xtal | clear | xtal | clear | xtal |
| C | 12 | 28 | clear | clear | xtal | clear | clear | clear | clear |

TABLE 3-continued

Epothilone D solubility in 10 mg/mL formulations with 60% ethanol and varying Tween® 80 and propylene glycol concentrations

| For- | % | % | Visual Appearance | | | | | | |
|---|---|---|---|---|---|---|---|---|---|
| | Tween | | | RODI | | D5W | | Saline | |
| mula-tion | 80 | PG | Initial | 1 h | 19 h | 1 h | 19 h | 1 h | 19 h |
| D | 13 | 27 | clear | clear | clear | clear | clear | clear | xtal |
| E | 14 | 26 | clear | clear | xtal | clear | xtal | clear | clear |
| F | 15 | 25 | clear | clear | xtal | clear | xtal | clear | clear |

Key: "ppt" = precipitation; "xtal" = crystallization

In another experiment, the effects of varying the proportions of Tween® 80 and ethanol with constant 40% propylene glycol (PG) in formulations containing 10 mg/mL of epothilone D were determined as shown in Table 4.

TABLE 4

Epothilone D solubility in 10 mg/mL formulations with 40% propylene glycol and varying Tween® 80 and ethanol concentrations

| For- | % | % | Visual Appearance | | | | | | |
|---|---|---|---|---|---|---|---|---|---|
| | Tween | | | RODI | | D5W | | Saline | |
| mula-tion | 80 | EtOH | Ini-tial | 1 h | 19 h | 1 h | 19 h | 1 h | 19 h |
| A | 10 | 50 | clear | clear | clear | clear | xtal | clear | clear |
| B | 11 | 49 | clear | clear | xtal | clear | xtal | clear | xtal |
| C | 12 | 48 | clear | clear | clear | clear | clear | clear | clear |
| D | 13 | 47 | clear | clear | clear | clear | clear | clear | clear |
| E | 14 | 46 | clear | clear | clear | clear | clear | clear | clear |
| F | 15 | 45 | clear | clear | clear | clear | clear | clear | xtal |

Key: "ppt" = precipitation; "xtal" = crystallization

In another experiment, the effects of varying the proportions of Tween® 80 and ethanol with constant 60% PEG400 in formulations containing 10 mg/mL of epothilone D were determined as shown in Table 5.

TABLE 5

Epothilone D solubility in 10 mg/mL formulations with 60% PEG400 and varying Tween® 80 and ethanol concentrations

| For- | % | % | Visual Appearance | | | | | | |
|---|---|---|---|---|---|---|---|---|---|
| | Tween | | | RODI | | D5W | | Saline | |
| mula-tion | 80 | EtOH | Initial | 1 h | 19 h | 1 h | 19 h | 1 h | 19 h |
| A | 10 | 30 | clear | clear | clear | clear | xtal | clear | clear |
| B | 11 | 29 | clear | clear | clear | clear | xtal | clear | clear |
| C | 12 | 28 | clear | clear | xtal | clear | clear | clear | clear |
| D | 13 | 27 | clear | clear | clear | clear | clear | clear | xtal |
| E | 14 | 26 | clear | clear | clear | clear | clear | clear | clear |
| F | 15 | 25 | clear | clear | xtal | clear | clear | clear | clear |

Key: "ppt" = precipitation; "xtal" = crystallization

In another experiment, the effects of varying the proportions of Tween® 80 and PEG400 (PEG) with constant 60% ethanol in formulations containing 10 mg/mL of epothilone D were determined as shown in Table 6.

TABLE 6

Epothilone D solubility in 10 mg/mL formulations with 60% ethanol (EtOH) and varying Tween ® 80 and PEG400 concentrations

| For-mula-tion | % Tween 80 | % PEG 400 | Visual Appearance | | | | | | |
|---|---|---|---|---|---|---|---|---|---|
| | | | RODI | | | D5W | | Saline | |
| | | | Initial | 1 h | 19 h | 1 h | 19 h | 1 h | 19 h |
| A | 10 | 30 | clear | clear | clear | clear | clear | clear | xtal |
| B | 11 | 29 | clear | clear | clear | clear | clear | clear | clear |
| C | 12 | 28 | clear | clear | clear | clear | clear | clear | clear |
| D | 13 | 27 | clear | clear | clear | clear | clear | clear | clear |
| E | 14 | 26 | clear | clear | clear | clear | clear | clear | clear |
| F | 15 | 25 | clear | clear | clear | clear | clear | clear | clear |

Key: "ppt" = precipitation; "xtal" = crystallization

In another experiment, the effects of varying the proportions of ethanol (EtOH) and glycerol (Glyc) with constant 10% Tween® 80 in formulations containing 10 mg/mL of epothilone D were determined as shown in Table 7.

TABLE 7

Epothilone D solubility in 10 mg/mL formulations with 10% Tween ® 80 and varying ethanol and glycerol concentrations

| For-mula-tion | % EtOH | % Glyc | Visual Appearance | | | | | | |
|---|---|---|---|---|---|---|---|---|---|
| | | | RODI | | | D5W | | Saline | |
| | | | Initial | 1 h | 19 h | 1 h | 19 h | 1 h | 19 h |
| A | 80 | 10 | clear | clear | xtal | clear | clear | clear | xtal |
| B | 70 | 20 | clear | clear | xtal | clear | clear | clear | xtal |
| C | 60 | 30 | clear | clear | xtal | clear | xtal | clear | xtal |
| D | 50 | 40 | ppt | — | — | — | — | — | — |
| E | 40 | 50 | ppt | — | — | — | — | — | — |
| F | 30 | 60 | ppt | — | — | — | — | — | — |
| G | 20 | 70 | ppt | — | — | — | — | — | — |
| H | 10 | 80 | ppt | — | — | — | — | — | — |

Key: "ppt" = precipitation; "xtal" = crystallization

In another experiment, the effects of varying the proportions of PEG400 (PEG) and glycerol (Glyc) with constant 10% Tween® 80 in formulations containing 10 mg/mL of epothilone D were determined as shown in Table 8.

TABLE 8

Epothilone D solubility in 10 mg/mL formulations with 10% Tween ® 80 and varying PEG400 and glycerol concentrations

| For-mula-tion | % PEG 400 | % Glyc | Visual Appearance | | | | | | |
|---|---|---|---|---|---|---|---|---|---|
| | | | RODI | | | D5W | | Saline | |
| | | | Initial | 1 h | 19 h | 1 h | 19 h | 1 h | 19 h |
| A | 80 | 10 | clear | clear | xtal | clear | xtal | clear | xtal |
| B | 70 | 20 | Imm | xtal | — | xtal | — | xtal | — |
| C | 60 | 30 | Imm | xtal | — | xtal | — | xtal | — |
| D | 50 | 40 | imm | xtal | — | xtal | — | xtal | — |
| E | 40 | 50 | imm | xtal | — | xtal | — | xtal | — |
| F | 30 | 60 | imm | xtal | — | xtal | — | xtal | — |
| G | 20 | 70 | imm | xtal | — | xtal | — | xtal | — |

Key: "ppt" = precipitation; "xtal" = crystallization; "imm" = immiscible

In another experiment, the solubility of 10 mg/mL epothilone D in compositions comprising 10% Tween® 80 and varying amounts of ethanol, PEG400, propylene glycol (PG), and/or glycerol (Glyc) were determined as shown in Table 9.

TABLE 9

Epothilone D solubility in 10 mg/mL formulations with 10% Tween ® 80 and varying ethanol, PEG400, and either propylene glycol (PG) or glycerol (Glyc) concentrations

| For-mula-tion | % EtOH | % PEG | % Other | Visual Appearance | | | | |
|---|---|---|---|---|---|---|---|---|
| | | | | | RODI | | Saline | |
| | | | | Initial | 1 h | 24 h | 1 h | 24 h |
| A | 60 | 30 | — | clear | clear | xtal | clear | clear |
| B | 55 | 30 | 5 PG | clear | clear | xtal | clear | clear |
| C | 50 | 30 | 10 PG | clear | clear | xtal | clear | clear |
| D | 60 | 25 | 5 PG | clear | clear | clear | clear | clear |
| E | 60 | 20 | 10 PG | clear | clear | clear | clear | clear |
| F | 55 | 30 | 5 Glyc | clear | clear | clear | clear | clear |
| G | 50 | 30 | 10 Glyc | clear | clear | clear | clear | clear |
| H | 60 | 25 | 5 Glyc | clear | clear | clear | clear | clear |
| I | 60 | 20 | 10 Glyc | clear | clear | clear | clear | clear |

Key: "ppt" = precipitation; "xtal" = crystallization

EXAMPLE 4

Dilution Stability

The dilution stability of epothilone D formulations at 8-20 mg/mL in various formulations was examined. A stock solution of epothilone D (100 mg/mL) was prepared in ethanol. Epothilone D formulations were prepared as listed in the following tables by addition of the requisite amount of ethanol, PEG400, 10% Tween® 80, and either propylene glycol or glycerol to the appropriate volume of the epothilone D stock solution. The solubility of epothilone D in each vial was observed visually following gentle swirling. Each formulation was syringe filtered through a 0.2 micron PVDF filter. Each formulation was subsequently diluted 1:8, 1:10, or 1:12 in reverse osmosis deionized water (RODI) or 0.9% saline. Visual observations were taken upon preparation, upon dilution, and both 1 and 24 hours after incubation at ambient temperature. Solutions either remained clear ("Clear") or precipitation ("ppt") or crystallization (xtal") was observed as indicated in Tables 10 and 11.

TABLE 10

Epothilone D solubility (mg/mL) in 10% Tween ® 80, 60% ethanol, 20% PEG400, and 10% glycerol

| Amt. epo D (mg per mL) | Initial | RODI Dilution | | | | | | Saline Dilution | | | | | |
|---|---|---|---|---|---|---|---|---|---|---|---|---|---|
| | | 1:08 | | 1:10 | | 1:12 | | 1:08 | | 1:10 | | 1:12 | |
| | | 0 h | 24 h | 0 h | 24 h | 0 h | 24 h | 1 h | 24 h | 1 h | 24 h | 1 h | 24 h |
| 8 | clear | clear | clear | clear | clear | clear | clear | clear | xtal | xtal | — | xtal | — |
| 10 | clear | clear | clear | clear | clear | clear | clear | clear | xtal | xtal | — | xtal | — |
| 12 | clear | clear | clear | clear | clear | clear | xtal | xtal | — | xtal | — | xtal | — |
| 16 | clear | ppt | — | ppt | — | ppt | — | ppt | — | ppt | — | ppt | — |
| 20 | clear | ppt | — | ppt | — | ppt | — | ppt | — | ppt | — | ppt | — |

Key: "ppt" = precipitation; "xtal" = crystallization

TABLE 11

Epothilone D solubility (mg/mL) in 10% Tween ® 80, 50% ethanol, 30% PEG400, and 10% propylene glycol.

| Amt. epo D (mg per mL) | Initial | RODI Dilution | | | | | | Saline Dilution | | | | | |
|---|---|---|---|---|---|---|---|---|---|---|---|---|---|
| | | 1:08 | | 1:10 | | 1:12 | | 1:08 | | 1:10 | | 1:12 | |
| | | 0 h | 24 h | 0 h | 24 h | 0 h | 24 h | 1 h | 24 h | 1 h | 24 h | 1 h | 24 h |
| 8 | clear | clear | clear | clear | clear | clear | clear | xtal | — | xtal | — | clear | xtal |
| 10 | clear | clear | clear | clear | clear | clear | clear | xtal | — | xtal | — | xtal | — |
| 12 | clear | clear | clear | clear | clear | clear | xtal | xtal | — | xtal | — | xtal | — |
| 16 | clear | ppt | — | ppt | — | ppt | — | ppt | — | ppt | — | ppt | — |
| 20 | clear | ppt | — | ppt | — | ppt | — | ppt | — | ppt | — | ppt | — |

Key: "ppt" = precipitation; "xtal" = crystallization

The dilution stability up to 48 hours post-dilution was examined for the above formulations containg 8-11 mg/mL of epothilone D after 1:10 dilution into either RODI water or 0.45% saline, as summarized in Tables 12 and 13 below.

TABLE 12

Epothilone D solubility (mg/mL) in 10% Tween ® 80, 60% ethanol, 20% PEG400, and 10% glycerol

| Amt. epo D, mg per mL | Initial | RODI Dilution | | | | | Saline Dilution | | | | |
|---|---|---|---|---|---|---|---|---|---|---|---|
| | | 0 h | 12 h | 24 h | 36 h | 48 h | 0 h | 12 h | 24 h | 36 h | 48 h |
| 8 | clear | clear | clear | clear | xtal | — | clear | xtal | — | — | — |
| 9 | clear | clear | clear | clear | xtal | — | clear | xtal | — | — | — |
| 10 | clear | clear | clear | clear | clear | xtal | clear | xtal | — | — | — |
| 11 | clear | clear | xtal | — | — | — | clear | xtal | — | — | — |

Key: "ppt" = precipitation; "xtal" = crystallization

TABLE 13

Epothilone D solubility (mg/mL) in 10% Tween ® 80, 50% ethanol, 30% PEG400, and 10% propylene glycol

| Amt. epo D, mg per mL | Visual Appearance | | | | | | | | | | |
|---|---|---|---|---|---|---|---|---|---|---|---|
| | Ini-tial | RODI Dilution | | | | | Saline Dilution | | | | |
| | | 0 h | 12 h | 24 h | 36 h | 48 h | 0 h | 12 h | 24 h | 36 h | 48 h |
| 8 | clear | clear | clear | clear | clear | clear | clear | xtal | — | — | — |
| 9 | clear | clear | clear | clear | clear | clear | clear | xtal | — | — | — |
| 10 | clear | clear | clear | clear | clear | clear | clear | clear | clear | xtal | — |
| 11 | clear | clear | xtal | — | — | — | clear | xtal | — | — | — |

Key: "ppt" = precipitation; "xtal" = crystallization

EXAMPLE 5

Formulations Comprising Solutol® HS-15

The solubility of epothilone D in three formulations comprising Solutol® HS-15 were examined. Three vehicles were prepared by combining appropriate amounts of excipients: (1) Vehicle A: 20% Solutol® HS-15, 30% PEG400, and 50% ethanol; (2) Vehicle C: 20% Solutol® HS-15, 20% PEG400, 10% propylene glycol, and 50% ethanol; and Vehicle D: 20% Solutol® HS-15, 10% PEG400, 20% propylene glycol, and 50% ethanol. Approximately 25 mg of epothilone D was weighed into each of three glass vials. Appropriate volumes of the three vehicles were added to the vials to give a final epothilone D concentration of 10 mg/mL to give formulations A, C, and D, respectively.

For dilution stability studies, the formulations were diluted at 1:10 and 1:5 using five different diluents: (1) water for injection (WFI); (2) 0.9% saline; (3) 0.45% saline; (4) 5% dextrose; and (5) 2.5% dextrose. The physical appearance of the diluted formulations was monitored over a 72 hour period, and the concentration and chromatographic purity of epothilone D in the water-diluted samples was determined by HPLC. The osmolarities of the diluted formulations were measured using a Vapro 5520 vapor pressure osmometer according to the manufacturer's recommended procedure. Osmolarities (mOsmol/kg) are given below in Table 14.

TABLE 14

Osmolarities of Solutol ® HS-15-containing formulations upon dilution

| Dilution | Concentration epo D (mg/mL) | Osmolarity (mOsmol/kg) | | |
|---|---|---|---|---|
| | | A | C | D |
| 1:10 WFI | 1.0 | 120 | 192 | 249 |
| 1:5 WFI | 2.0 | 290 | 489 | 581 |
| 1:10 0.9% Saline | 1.0 | 412 | 513 | — |
| 1:10 0.45% saline | 1.0 | 271 | 364 | — |
| 1:10 5% dextrose | 1.0 | 402 | 500 | — |
| 1:10 2.5% dextrose | 1.0 | 254 | 348 | — |

TABLE 15

Visual appearance of Solutol ® HS-15-containing formulations upon dilution after 0, 24, and 48 hours

| Dilution | Conc. epo mg per mL | Visual Appearance | | | | | | | | |
|---|---|---|---|---|---|---|---|---|---|---|
| | | A | | | C | | | D | | |
| | | 0 h | 24 h | 48 h | 0 h | 24 h | 48 h | 0 h | 24 h | 48 h |
| 1:10 WFI | 1.0 | clear | clear | clear | clear | clear | clear | clear | clear | xtal |
| 1:5 WFI | 2.0 | clear | clear | clear | clear | clear | clear | clear | clear | xtal |
| 1:10 0.9% saline | 1.0 | clear | clear | clear | clear | clear | clear | clear | clear | — |
| 1:10 0.45% saline | 1.0 | clear | clear | clear | clear | clear | clear | clear | clear | — |
| 1:10 5% dextrose | 1.0 | clear | clear | clear | clear | clear | clear | clear | clear | — |
| 1:10 2.5% dextrose | 1.0 | clear | clear | clear | clear | clear | clear | clear | clear | — |

Key: "ppt" = precipitation; "xtal" = crystallization

TABLE 16

Epothilone D concentration in Solutol ® HS-15-containing formulations upon 1:10 or 1:5 dilution into water after 0, 8, and 24 h

| Dilution | Epothilone D concentration (mg/mL) | | |
|---|---|---|---|
| | 0 h | 8 h | 24 h |
| A 1:10 | 1.13 | 1.12 | 1.11 |
| A 1:5 | 2.15 | 2.11 | 2.12 |

TABLE 16-continued

Epothilone D concentration in Solutol ® HS-15-containing formulations upon 1:10 or 1:5 dilution into water after 0, 8, and 24 h

| Dilution | Epothilone D concentration (mg/mL) | | |
|---|---|---|---|
| | 0 h | 8 h | 24 h |
| C 1:10 | 1.11 | 1.09 | 1.11 |
| C 1:5 | 2.19 | 2.14 | 2.2 |
| D 1:10 | 1.11 | 1.08 | — |
| D 1:5 | 2.17 | 2.07 | — |

TABLE 17

Chromatographic purity of epothilone D in Solutol ® HS-15-containing formulations upon 1:10 or 1:5 dilution into water after 0, 8, and 24 hours

| Dilution | % Epothilone D peak area | | |
|---|---|---|---|
| | 0 h | 8 h | 24 h |
| A 1:10 | 98.56 | 98.55 | 98.51 |
| A 1:5 | 98.64 | 98.65 | 98.61 |
| C 1:10 | 98.53 | 98.85 | 98.49 |
| C 1:5 | 98.64 | 98.64 | 98.60 |
| D 1:10 | 98.50 | 98.48 | — |
| D 1:5 | 98.55 | 98.58 | — |

These results of Tables 14-17 demonstrate that formulations comprising epothilone D at 10 mg/mL in vehicles A and C provide 1:10 and 1:5 dilution solutions that are stable for at least 48 hours at ambient temperature. The purity of the epothilone D in these dilutions remained greater than 98% after 48 hours at ambient temperature.

Certain embodiments of the invention having been illustrated by the above examples, it will be apparent to those skilled in the arts of pharmacology and medicine that many alternative embodiments of the invention not explicitly described herein are nevertheless encompassed by the invention. Further, while the present invention has been particularly described in terms of certain preferred embodiments, the invention is not limited to such preferred embodiments. Rather, the scope of the invention is defined by the appended claims.

All references not explicitly incorporated by reference are herein incorporated by reference in their entireties.

What is claimed is:

1. A pharmaceutical composition comprising a homogeneous solution of a desoxyepothilone together with a pharmaceutically acceptable carrier, wherein said pharmaceutically acceptable carrier comprises ethanol at between about 40% and about 70%, glycerol at between about 5% and about 15%, PEG 400 at between about 10% and about 40%, and polysorbate 80 at between about 5% and about 15%, wherein said desoxyepothilone is present at between about 0.1 mg/mL and about 100 mg/mL, and wherein the pharmaceutical composition provides physically and chemically stable solutions before and after dilution into aqueous medium.

2. The pharmaceutical composition of claim 1, wherein said pharmaceutically acceptable carrier comprises ethanol at about 60%, glycerol at about 10%, PEG 400 at about 20%, and polysorbate 80 at about 10%.

3. The pharmaceutical composition of claim 2, wherein the desoxyepothilone is epothilone D at between about 1 mg/mL and about 20 mg/mL.

4. The pharmaceutical composition of claim 2, wherein the desoxyepothilone is epothilone D at between about 1 mg/mL and about 10 mg/mL.

5. The pharmaceutical composition of claim 2, wherein the desoxyepothilone is epothilone D at about 10 mg/mL.

6. A pharmaceutical composition comprising a homogeneous solution of a desoxyepothilone together with a pharmaceutically acceptable carrier, wherein said pharmaceutically acceptable carrier comprises ethanol at between about 40% and about 70%, propylene glycol at between about 5% and about 15%, PEG400 at between about 10% and about 40%, and polysorbate 80 at between about 5% and about 15%, wherein said desoxyepothilone is present at between about 1 mg/mL and about 100 mg/mL, and wherein the pharmaceutical composition provides physically and chemically stable solutions before and after dilution into aqueous medium.

7. The pharmaceutical composition of claim 6, wherein said pharmaceutically acceptable carrier comprises ethanol at about 50%, propylene glycol at about 10%, PEG400 at about 30%, and polysorbate 80 at about 10%.

8. The pharmaceutical composition of claim 7, wherein the desoxyepothilone is epothilone D at between about 1 mg/mL and about 20 mg/mL.

9. The pharmaceutical composition of claim 7, wherein the desoxyepothilone is epothilone D at between about 1 mg/mL and about 10 mg/mL.

10. The pharmaceutical composition of claim 7, wherein the desoxyepothilone is epothilone D at about 10 mg/mL.

11. A pharmaceutical composition comprising a homogeneous solution of a desoxyepothilone together with a pharmaceutically acceptable carrier, wherein said pharmaceutically acceptable carrier comprises ethanol at between about 40% and about 70%, PEG400 at between about 10% and about 40%, and Solutol HS-15 at between about 10% and about 30%, wherein said desoxyepothilone is present at between about 1 mg/mL and about 100 mg/mL, and wherein the pharmaceutical composition provides physically and chemically stable solutions before and after dilution into aqueous medium.

12. The pharmaceutical composition of claim 11, wherein said pharmaceutically acceptable carrier comprises ethanol at about 50%, PEG400 at about 30%, and Solutol HS-15 at about 20%.

13. The pharmaceutical composition of claim 12, wherein the desoxyepothilone is epothilone D at between about 1 mg/mL and about 20 mg/mL.

14. The pharmaceutical composition of claim 12, wherein the desoxyepothilone is epothilone D at between about 1 mg/mL and about 10 mg/mL.

15. The pharmaceutical composition of claim 12, wherein the desoxyepothilone is epothilone D at about 10 mg/mL.

* * * * *